United States Patent [19]

Yamate

[11] Patent Number: Plant 6,826

[45] Date of Patent: May 30, 1989

[54] CHRYSANTHEMUM NAMED REGATTA

[75] Inventor: Yoshihiko Yamate, Kanemaru, Japan

[73] Assignee: Chrysanthemum Breeders Association, N.V., Curacao, Netherlands Antilles

[21] Appl. No.: 141,269

[22] Filed: Jan. 6, 1988

[51] Int. Cl.[4] ..... A01H 5/00

[52] U.S. Cl. ..... Plt./74

[58] Field of Search ..... Plt./74

*Primary Examiner*—Robert E. Bagwill

*Attorney, Agent, or Firm*—Parkhurst, Oliff & Berridge

[57] ABSTRACT

A new and distinct cultivar of Chrysanthemum plant named Regatta, bearing medium sized yellow blooms with a green center and a performance of 20 days.

3 Drawing Sheets

BACKGROUND OF THE NEW PLANT

The new plant of the present invention relates to the Chrysanthemum genus.

ORIGIN AND HISTORY OF THE NEW PLANT

The new plant according to the present invention comprises a new and distinct cultivar of chrysanthemum plant which is a crossbreed of unknown parents. The new cultivar was discovered by Yoshihiko Yamate at Kanemaru Shinichi-Cho, Ashina-Gun, Hiroshima, Japan. The new cultivar has been asexually reproduced by cuttings at the same location, and has been found to retain its distinctive characteristics through successive propagations.

SUMMARY OF THE NEW PLANT

The present invention is a new and distinct variety of chrysanthemum of a medium sized bloom and yellow color.

BRIEF DESCRIPTION OF THE DRAWINGS

The present new and distinct Chrysanthemum cultivar is shown in the accompanying drawings, the color being as nearly true as possible with color photographs of this type.

Sheet 1 shows the full bloom of the new cultivar;

Sheet 2 shows various stages of bloom of the new cultivar; and

Sheet 3 shows the foliage and petiole of the new cultivar.

DESCRIPTION OF THE NEW PLANT

This new variety of chrysanthemum is of the botanical classification *Chrysanthemum morifolium,* named Regatta. When grown in the vicinity of Ter Aar, Holland, it has a response time of approximately nine (9) weeks. This new variety produces medium sized yellow blooms with a green center having a performance of 20 days. This new variety of Chrysanthemum has been found to retain its distinctive characteristics throughout successive propagations and may be planted under conventional greenhouse conditions in Holland between weeks five and thirty-two (5 and 32).

The following is a description of the plant and characteristics that distinguish it over related known varieties and its antecedents:

Botanical classification: *Chrysanthemum morifolium.*

Bud:
- *Size.*—Small (cross section: 1.0 cm height: 0.9 cm).
- *Form.*—Round and a flat top.
- *Outside color.*—Yellow orange 17A.

Bloom:
- *Size.*—Medium.
- *Fully expanded.*—8 cm.
- *Borne.*—Single.
- *Stems.*—Strong, thick.
- *Form.*—Anemone type.
- *Permanence.*—Good, 20 days (at 18°-20° C.).

Color:
- *Center of flower (Disk Floret).*—The cushion: yellow orange 22A. The green spot in the middle: Green 135A.
- *Base of petals.*—Yellow orange 21A.
- *Inside of petals.*—Yellow orange 20A.
- *Reverse of petals.*—Yellow orange 20A.
- *Outer petals.*—Yellow orange 20A.
- *Tonality from a distance: A yellow anemone with a fresh looking green spotted center.*
- *Discoloration.*—May discolor some to yellow orange 20B at maturity.

Petals:
- *Texture.*—Upperside: Smooth. Underside: Smooth.
- *Number.*—24-28.
- *Cross-section.*—Somewhat concave, two keels.
- *Arrangement.*—Imbricated.
- *Persistence.*—Some reflexion at the edge when overblooming.
- *Fragrance.*—Typical Chrysanthemum.

Reproductive organs:
- *Stamens.*—Yellow thin, length: 3 mm.
- *Pollen.*—Yes, some in the petals of the cushion.
- Styles.—Green, thin, length: 6 mm.
- *Stigmas.*—Yellow, width: 0.8 cm.
- Ovaries.—Enclosed in calyx.

Plant:
- *Form.*—Spray mum meant for erect culture. Herbaceous.
- *Growth.*—Medium.
- *Height.*—90-95 cm.
- *Peduncle.*—Near the top: 10 cm. Near the middle: 15 cm. Near the bottom: 21 cm.
- *Internodes.*—2 cm.
- *Flowering response.*—Nine (9) weeks.

Foliage:
- *Color.*—Upperside: Green 147A. Underside: Green 148A.

*Size.*—Length: 11 cm. Width: 9.5 cm.
*Quantity.*—40.
*Shape.*—Oval, deeply undulated.
*Texture.*—Upperside: Rough. Underside: Smooth, slightly hirsute.
*Ribs and veins.*—Ribs and veins well developed. Upperside: Ribs and veins well defined. Underside: Ribs and veins well defined.
*Edge.*—Crenated.

In the description above, color references are made to the "R.H.S. Colour Chart" issued by The Royal Horticultural Society, in association with the Flower Council of Holland, Edition February 1986.

What is claimed:

1. A new and distinct cultivar of Chrysanthemum named Regatta, and parts thereof, as described and illustrated in the foregoing specification and accompanying drawings.

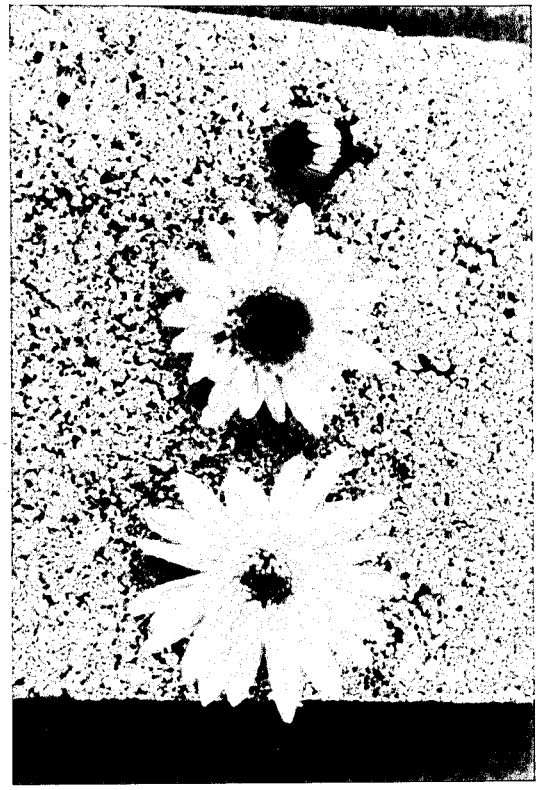

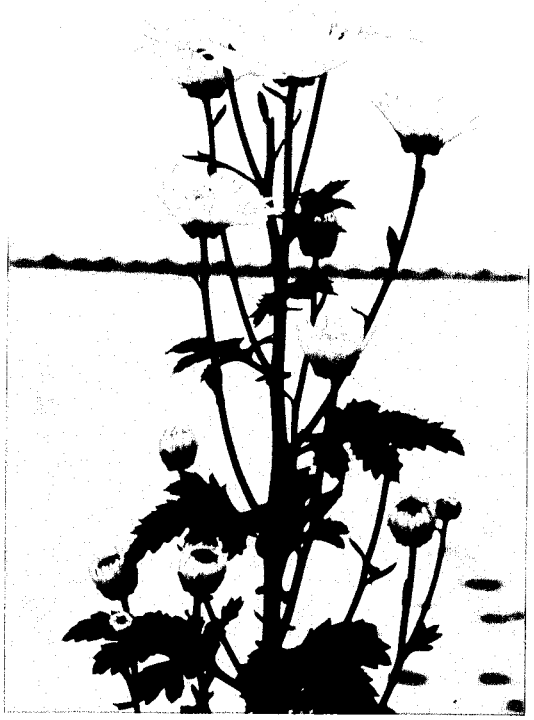

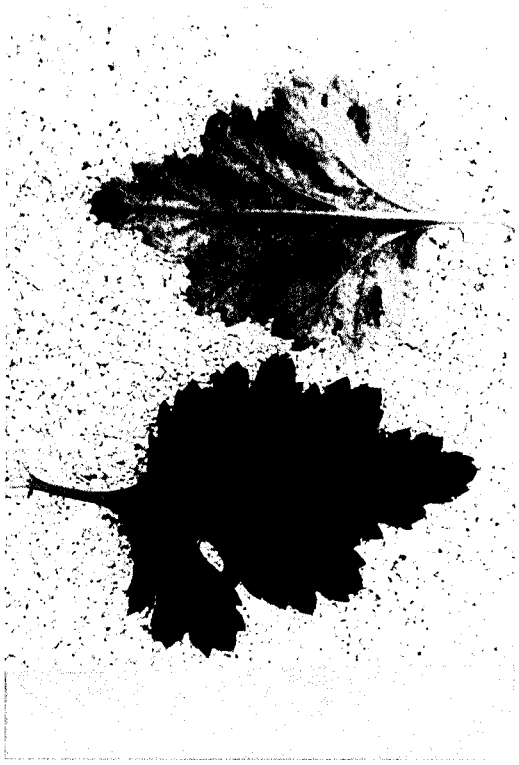

* * * * *